(12) United States Patent
Hansen et al.

(10) Patent No.: US 8,613,731 B2
(45) Date of Patent: Dec. 24, 2013

(54) MEDICAL DELIVERY SYSTEM WITH ASYMMETRICAL CODING MEANS

(75) Inventors: Michael Ejstrup Hansen, Morud (DK); Søren Steenfeldt-Jensen, Hornbaek (DK); Thomas Pedersen, Helsingoer (DK); Claus Schmidt Møller, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 538 days.

(21) Appl. No.: 12/373,339

(22) PCT Filed: Jul. 15, 2007

(86) PCT No.: PCT/EP2007/057282
§ 371 (c)(1),
(2), (4) Date: Jan. 12, 2009

(87) PCT Pub. No.: WO2008/009645
PCT Pub. Date: Jan. 24, 2008

(65) Prior Publication Data
US 2009/0281505 A1    Nov. 12, 2009

Related U.S. Application Data

(60) Provisional application No. 60/837,809, filed on Aug. 14, 2006, provisional application No. 60/899,197, filed on Feb. 2, 2007.

(30) Foreign Application Priority Data

Jul. 15, 2006 (EP) ..................................... 06014770
Jan. 10, 2007 (EP) ..................................... 07000430

(51) Int. Cl.
*A61M 5/00* (2006.01)

(52) U.S. Cl.
USPC ........... 604/242; 604/208; 604/207; 604/181; 604/187

(58) Field of Classification Search
USPC ........... 604/208, 240, 90, 523, 207, 218, 191, 604/209–211, 181, 187; 285/376
See application file for complete search history.

(56) References Cited

U.S. PATENT DOCUMENTS 1,594,493 A  8/1926  Brown
2,020,828 A  11/1935 Goldberg
(Continued)

FOREIGN PATENT DOCUMENTS

CH  0315980  9/1956
CH  0501411  1/1971
(Continued)

OTHER PUBLICATIONS

English Language Abstract of German Patent Publication No. DE20110690, published Sep. 13, 2001.
(Continued)

*Primary Examiner* — Emily Schmidt
*Assistant Examiner* — Bradley G Thomas, Jr.
(74) *Attorney, Agent, or Firm* — Wesley A. Nicolas; Marc A. Began; Reza Green

(57) ABSTRACT

A dosing assembly (204) and/or a container (202) comprising fastening means (206,208) for fastening the container to the dosing assembly, the fastening means of the dosing assembly and/or the container defining an asymmetrical pattern in a plane transverse to an axial direction of the dosing assembly and/or a container.

17 Claims, 7 Drawing Sheets

(56) References Cited

U.S. PATENT DOCUMENTS

Figure 1:
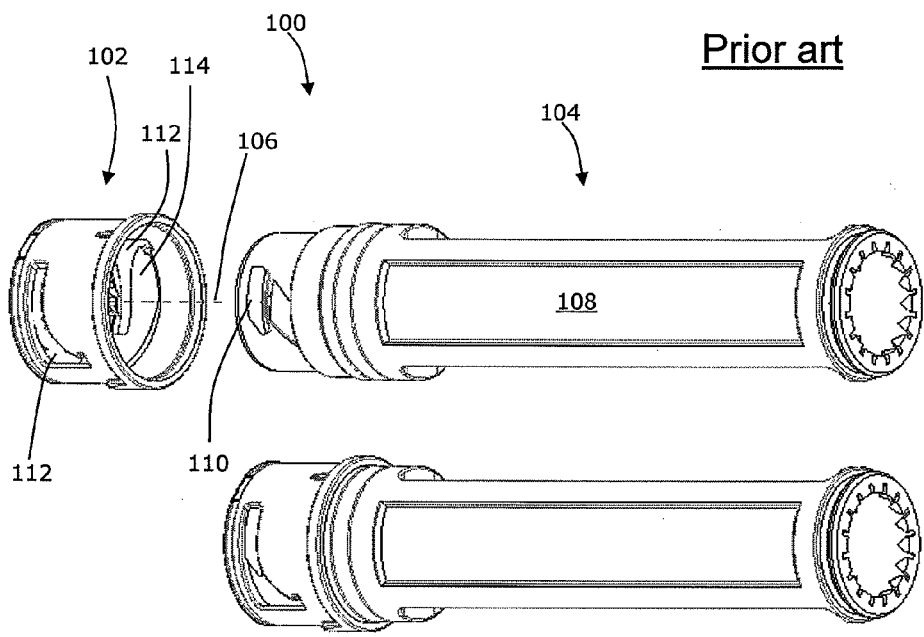

| | | |
|---|---|---|
| 2,707,466 A | 5/1955 | Hoskins |
| 2,818,864 A | 1/1958 | Hudson |
| 2,865,372 A | 12/1958 | Miskel et al. |
| 2,880,723 A | 4/1959 | Adams |
| 2,888,924 A | 6/1959 | Dunmire |
| 3,021,840 A | 2/1962 | Hallamore et al. |
| 3,130,724 A | 4/1964 | Higgins et al. |
| 3,130,742 A | 4/1964 | Bredtschneid |
| 3,170,667 A | 2/1965 | Szohatzky |
| 3,336,924 A | 8/1967 | Sarnoff et al. |
| 3,375,825 A | 4/1968 | Keller |
| 3,820,652 A | 6/1974 | Thackston |
| 3,831,599 A | 8/1974 | Needham |
| 3,895,633 A | 7/1975 | Bartner et al. |
| 3,916,893 A | 11/1975 | De Felice |
| 3,989,044 A | 11/1976 | Meierhoefer |
| 4,089,432 A | 5/1978 | Crankshaw |
| 4,150,673 A | 4/1979 | Watt |
| 4,280,723 A | 7/1981 | Moldestad |
| 4,490,142 A | 12/1984 | Silvern |
| RE31,873 E | 4/1985 | Howes |
| RE31,878 E | 5/1985 | Ritsema |
| 4,592,745 A | 6/1986 | Rex et al. |
| 4,619,640 A | 10/1986 | Potolsky et al. |
| 4,619,651 A | 10/1986 | Kopfer et al. |
| 4,664,656 A | 5/1987 | Taddei |
| 4,685,314 A | 8/1987 | Greenwalt et al. |
| 4,693,833 A | 9/1987 | Toshikuni et al. |
| 4,740,205 A | 4/1988 | Seltzer |
| 4,768,568 A | 9/1988 | Fournier et al. |
| 4,781,701 A | 11/1988 | Geprags |
| 4,944,736 A | 7/1990 | Holtz |
| 4,948,000 A | 8/1990 | Grobenkort |
| 4,973,318 A | 11/1990 | Holm et al. |
| 4,976,701 A | 12/1990 | Ejlersen et al. |
| 5,000,744 A | 3/1991 | Hoffman et al. |
| 5,002,537 A | 3/1991 | Hoffman et al. |
| 5,017,190 A | 5/1991 | Simon et al. |
| 5,084,017 A | 1/1992 | Maffetone |
| 5,205,833 A | 4/1993 | Harsh et al. |
| 5,226,896 A | 7/1993 | Harris |
| 5,244,465 A | 9/1993 | Michel |
| 5,269,317 A | 12/1993 | Bennett |
| 5,286,258 A * | 2/1994 | Haber et al. ............... 604/90 |
| 5,458,580 A | 10/1995 | Hajishoreh |
| 5,478,323 A * | 12/1995 | Westwood et al. ......... 604/191 |
| 5,498,253 A | 3/1996 | Aswad et al. |
| 5,554,134 A | 9/1996 | Bonnichsen |
| 5,584,815 A | 12/1996 | Pawelka et al. |
| 5,611,783 A * | 3/1997 | Mikkelsen ................. 604/208 |
| 5,693,027 A | 12/1997 | Hansen et al. |
| 5,743,889 A | 4/1998 | Sams |
| 5,938,642 A | 8/1999 | Burroughs et al. |
| 5,954,700 A | 9/1999 | Kovelman |
| 5,957,896 A * | 9/1999 | Bendek et al. ............. 604/207 |
| 6,017,330 A | 1/2000 | Hitchens et al. |
| 6,197,040 B1 | 3/2001 | LeVaughn et al. |
| 6,582,399 B1 | 6/2003 | Smith et al. |
| 6,582,408 B1 | 6/2003 | Buch-Rasmussen et al. |
| 6,648,859 B2 | 11/2003 | Bitdinger et al. |
| 7,604,619 B2 * | 10/2009 | Eich et al. ................. 604/232 |
| 2001/0047153 A1 | 11/2001 | Trocki et al. |
| 2002/0016571 A1 | 2/2002 | Kirchhofer et al. |
| 2002/0099360 A1 | 7/2002 | Bierman |
| 2002/0169470 A1 | 11/2002 | Kuhr et al. |
| 2003/0004466 A1* | 1/2003 | Bitdinger et al. ........... 604/218 |
| 2003/0078195 A1 | 4/2003 | Kristensen et al. |
| 2004/0210199 A1 | 10/2004 | Atterbury |
| 2004/0215152 A1 | 10/2004 | Kirchhofer et al. |
| 2004/0238776 A1 | 12/2004 | Peters et al. |
| 2006/0153693 A1 | 7/2006 | Fiechter et al. |
| 2008/0051713 A1 | 2/2008 | Kohlbrenner |

FOREIGN PATENT DOCUMENTS

| | | |
|---|---|---|
| DE | 2137405 | 2/1973 |
| DE | 44 19 235 | 12/1995 |
| DE | 20110690 | 9/2001 |
| EP | 217055 | 4/1987 |
| EP | 0 549 694 | 7/1993 |
| EP | 762311 | 3/1997 |
| EP | 774270 | 5/1997 |
| EP | 897729 | 2/1999 |
| EP | 897728 | 5/2003 |
| GB | 301961 | 12/1928 |
| GB | 1205201 | 9/1970 |
| GB | 1437595 | 5/1976 |
| GB | 1525455 | 9/1978 |
| GB | 2214819 | 9/1989 |
| WO | WO89/02760 | 4/1989 |
| WO | WO 90/09202 | 8/1990 |
| WO | WO92/04926 | 4/1992 |
| WO | WO98/47559 | 10/1998 |
| WO | WO98/56438 | 12/1998 |
| WO | WO00/02605 | 1/2000 |
| WO | WO00/35519 | 6/2000 |
| WO | WO 01/72361 | 10/2001 |
| WO | WO 02/30490 | 4/2002 |
| WO | WO 03/011372 | 2/2003 |
| WO | WO 03/011373 | 2/2003 |
| WO | WO03/017915 | 3/2003 |
| WO | WO2006/069456 | 7/2006 |
| WO | WO 2008/009646 | 1/2008 |

OTHER PUBLICATIONS

Search Report from International Application No. PCT/EP2007/062661, mailed Feb. 25, 2008.
Non-final Office Action in U.S. Appl. No. 12/374,600, sent from the USPTO on Jan. 19, 2010.
Non-Final Office Action Mailed Mar. 4, 2011 in U.S. Appl. No. 12/374,600, filed Jan. 21, 2009 by Christiansen.
Novo Nordisk Product Brochure for Insuject-X 1987.
Non-Final Office Action Mailed Apr. 9, 2004 in U.S. Appl. No. 10/230,428, filed Aug. 23, 2002; First Named Inventor: Kristensen.
Non-Final Office Action Mailed Nov. 18, 2004 in U.S. Appl. No. 10/230,428, filed Aug. 23, 2002; First Named Inventor: Kristensen.
Notice of Allowance Mailed May 19, 2005 in U.S. Appl. No. 10/230,428, filed Aug. 23, 2002; First Named Inventor: Kristensen.
Non-Final Office Action Mailed Feb. 9, 2006 in U.S. Appl. No. 10/230,428, filed Aug. 23, 2002; First Named Inventor: Kristensen.
Notice of Allowance Mailed Oct. 10, 2006 in U.S. Appl. No. 10/230,428, filed Aug. 23, 2002; First Named Inventor: Kristensen.
Non-Final Office Action Mailed Dec. 12, 2006 in U.S. Appl. No. 10/230,428, filed Aug. 23, 2002; First Named Inventor: Kristensen.
Non-Final Office Action Mailed Feb. 10, 2009 in U.S. Appl. No. 11/784,738, filed Apr. 9, 2007; First Named Inventor Kristensen.
Final Office Action Mailed Jun. 2, 2009 in U.S. Appl. No. 11/784,738, filed Apr. 9, 2007; First Named Inventor Kristensen.
Final Office Action Mailed Aug. 12, 2010 in U.S. Appl. No. 12/522,566, filed Sep. 2, 2009; First Named Inventor: Kristensen.
Notice of Allowance Mailed Dec. 13, 2010 in U.S. Appl. No. 12/522,566, filed Sep. 2, 2009; First Named Inventor: Kristensen.
Non-Final Office Action Mailed Oct. 29, 2010 in U.S. Appl. No. 12/305,684, filed Dec. 19, 2008; First Named Inventor: Steenfeldt-Jensen.
Non-Final Office Action Mailed Feb. 18, 2011 in U.S. Appl. No. 12/373,340, filed Jan. 12, 2009 by Christiansen.
Non-Final Office Action Mailed Feb. 17, 2011 in U.S. Appl. No. 12/357,013, filed Jan. 21, 2009 by Christiansen.
Final Office Action Mailed Jul. 15, 2010 in U.S. Appl. No. 12/374,600, filed Jan. 21, 2009 by Christiansen.

* cited by examiner

MEDICAL DELIVERY SYSTEM WITH ASYMMETRICAL CODING MEANS

CROSS-REFERENCE TO RELATED APPLICATIONS

This application is a 35 U.S.C. §371 national stage application of International Patent Application PCT/EP2007/057282 (published as WO 2008/009645), filed Jul. 15, 2007, which claimed priority of European Patent Applications 06014770.9, filed Jul. 15, 2006 and 07000430.4, filed Jan. 10, 2007; this application further claims priority under 35 U.S.C. §119 of U.S. Provisional Applications 60/837,809, filed Aug. 14, 2006 and 60/899,197, filed Feb. 2, 2007.

FIELD OF THE INVENTION

The present invention relates to a medical delivery system comprising a container for accommodation of a medicament and a dosing assembly adapted to be fastened to the container. In particular the present invention relates to a first fastening means of the dosing assembly and/or a second fastening means of the container defining an asymmetrical pattern in a plane transverse to an axial direction of the device. Furthermore, the present invention relates to a container and a dosing assembly each of which are suitable for use in the medical delivery system according to the present invention.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and, thus, the delivery system to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding systems have been developed which primarily relies on the electronic reading and recognition of specific containers in order to allow delivery of a specific type of a medicament by a dedicated delivery device. The following mechanical coding systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotable when mounted with a cartridge in the syringe. In some types of syringes such keyed engagement between cartridge and syringe is further used to ensure that only a certain type of cartridge is used.

U.S. Pat. No. 6,648,859 B2 discloses a drug cartridge assembly for use with a reuseable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

Yet another prior art system is described in DE 201 10 690.

It is an object of a preferred embodiment of the present invention to provide an alternative to the known systems. Furthermore, it is an object of a preferred embodiment of the present invention to provide a medication delivery system with a large number of possible coding geometries.

Furthermore, it is an object of a preferred embodiment of the present invention to provide a coding system wherein the user experiences substantially the same operational fastening movement when the container and dosing assembly of a predetermined medical delivery system are coupled/uncoupled to each other regardless of the specific choice among sets of compatible containers and dosing assemblies. Additionally, it is an object of a preferred embodiment of the present invention to provide a system having a large number of differently coded containers/dosing assemblies while simultaneously obtaining a rugged system where the possibility of mechanical failure is minimized Furthermore, it is an object of a preferred embodiment of the present invention to provide an intuitive fastening mechanism for fastening the container to the dosing assembly.

BRIEF DESCRIPTION OF THE INVENTION

In a FIRST aspect the present invention relates to a medical delivery system comprising:
a container adapted to contain a medicament in a chamber defined by the container and a slidably arranged piston which is moveable in a distal direction towards an outlet so as to reduce the volume of the chamber and expel the medicament through the outlet;
a dosing assembly adapted to be fastened to the container, so as to allow a driver of the dosing assembly to move the piston of the container in the distal direction;
wherein the dosing assembly defines a first fastening means which during fastening of the container to the dosing assembly engages a second fastening means of the container whereby the container is fastened to the dosing assembly through a predetermined movement defined by at least one of the first and the second fastening means, the predetermined movement being less than one revolution;

wherein a sidewall of one of the first and second fastening means defines at least two projections extending in a radial direction, each of the at least two projections being adapted to engage a corresponding groove defined in a sidewall of the other one of the first and second fastening means; and wherein at least one of the first and second fastening means defines an asymmetrical pattern in a plane transverse to an axial direction of the device.

The medical system according to the present invention improves user safety as only predetermined containers may be attached to the dosing assembly. Thus, the dosing assembly may be designated to be used with a predetermined kind and/or concentration of a medicament, whereby containers accommodating other concentrations or types of medicaments cannot be attached to the dosing assembly.

In the context of the present invention the term "medical delivery system" shall be understood as any system capable of administering a medicament-containing flowable drug. Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle in a controlled manner, such as a liquid, solution, gel or fine suspension. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber of the container may be defined by one or more sidewalls of the container and the slidably arranged piston. In most embodiments at least a part of the container is ring-shaped and defines a cylindrical cavity in which the piston is received. The distal end of the container may comprise a seal for penetration by a cannula so as to allow a medicament contained in the chamber to be expelled through the cannula. The distal end of the container may be adapted to be attached to a holder holding a cannula. As an example the distal end of the container may comprise a thread adapted to cooperate with a corresponding thread of the holder so as to allow the holder to be screwed onto the container.

The outlet of the container may be adapted to cooperate with or be defined by a cannula or a needle or a needle hub or an infusion set, or any other fluid communicating conduit e.g. defined by a cannula or a needle, adapted to provide fluid access to a medicament accommodated in the container.

The driver of the dosing assembly may comprise a piston rod adapted to move the piston in the distal direction. The piston rod may comprise an element which is more rigid than the piston and is adapted to abut at least a part of and preferably most of the proximal facing surface of the piston whereby a force applied by the piston rod to the rigid element is applied to a larger area of the proximal surface of the piston than if the piston rod had engaged the piston directly.

The dosing assembly defines a first fastening means which during fastening of the container to the dosing assembly engages a second fastening means of the container. In one embodiment a proximal facing surface of the first fastening means of the dosing assembly engages a distal facing surface of the second fastening means of the container.

The container may be fastened to the dosing assembly through a predetermined movement comprising at least a concurrent axial and rotational movement, such as a helical movement. The rotational movement incurred by the concurrent axial and rotational movement is less than one revolution, such as less than 120 degrees, such as less than 90 degrees, such as less than 60 degrees. When the proximal facing surface of the first fastening means and the distal facing surface of the second fastening means are brought into engagement, rotation of the container relative to the dosing assembly causes the container and the dosing assembly to be pulled towards each other.

In a first embodiment the first fastening means of the dosing assembly defines a groove adapted to receive a projection defined by the second fastening means of the container. During fastening of the container to the dosing assembly, a substantially proximal facing surface of the first fastening means of the dosing assembly engages a substantially distal facing surface of the container. The predetermined movement is defined by the shape of at least one of the engaging surfaces. In a further embodiment, the second fastening means defines a plurality of projections such as two, three or four, and the first fastening means defines a corresponding plurality of grooves adapted to be engaged by the projections.

In a second embodiment the groove(s) is/are defined by the container and the projection(s) is/are defined by the dosing assembly. In a third embodiment the container defines a combination of grooves and projections adapted to be engaged by corresponding projections and grooves defined by the dosing assembly.

In the context of the present invention the term "asymmetrical pattern" shall be understood such that when the first and second fastening means define an asymmetrical pattern, there exist only one relative rotational position between the dosing assembly and the container, wherein the first fastening means may be received in/by the second fastening means so as to allow the container to be fastened to the dosing assembly. The relative rotational position of the container and the dosing assembly being relative to the longitudinal axis of the device.

In one embodiment the cross-section may be at right angle to the axial direction of the device, i.e. define an angle of 90 degrees relative to the axial direction of the device.

The pattern may be defined by the at least two projections and/or the at least two grooves, and thus the plane may extend through all of the at least two projections and/or all of the at least two grooves.

In one embodiment both the first and second fastening means defines an asymmetrical pattern in the plane transverse to the axial direction of the device. In said embodiment the cross sectional pattern of the first and the second fastening means may be substantially identical.

In one embodiment at least one of the first and second fastening means defines less than two lines of symmetry in the plane transverse to the axial direction of the device, such as one line of symmetry. In a particular embodiment the first and/or second fastening means defines one single line of symmetry extending a groove or projection of the first or second fastening means.

Moreover, at least one of the first and second fastening means may define no line of symmetry in the plane transverse to the axial direction of the device.

In a further embodiment, each of the at least two projections or grooves defines a centre point, and the angle between any two centre points about the longitudinal axis of the device, is different from 180 degrees. The centre point of a projection may be defined as the centre of inertia of the projection itself i.e. not taking into account the area of the remaining part of the cross-section. Additionally, the centre point of the groove may be defined as the centre of inertia of the mass/area removed to define the groove. Accordingly, in this embodiment any two projections/grooves are not positioned directly opposite each other on an inner or outer surface of the dosing assembly.

Moreover, the circumferential extent of two or more of the at least two projections or grooves may be different. By circumferential extent is meant the length of the projections/grooves along the circumference of the dosing assembly or container. In one embodiment the circumferential extent of a first projection is 50 percent larger than the circumferential extent of a second projection, such as 100 percent larger, such as 150 percent larger. Moreover, a first of the at least two projections or grooves may define a shape different from a second of the at least two projections or grooves.

In one embodiment one or more of the at least two projections or grooves may define an inclined surface such as relative to the axial direction of the device. The inclined surface may define a plane which extends transverse to the longitudinal direction of the device and at an angel different from 90 degrees relative to said longitudinal axis.

The medical delivery system may comprise an axially extending coding mechanism defined by a proximal end surface of the container and a corresponding distal end surface of the dosing assembly, the proximal end surface of the container defining one or more axially extending protrusions and/or indentations which during fastening of the container to the dosing assembly cooperate(s) with matching one or more protrusions and/or indentations of a distal facing coding surface of the dosing assembly so as to prevent said predetermined movement unless each of the distal and proximal facing surfaces define one or more predetermined protrusions and/or indentations selected from a predetermined group of protrusions and/or indentations. The proximal surface may be a proximal end surface. The distal surface may by a distal end surface. In one embodiment the end surface may be ring-shaped.

In the context of the present invention the terms "groove" and "projection" are only used in connection with the first and second fastening means, and "indentation" and "protrusion" are only used in connection with the axially extending coding mechanism. However, "groove" and "indentation" shall be seen as synonyms and "protrusion" and "projection" shall be seen as synonyms.

The axially extending coding mechanism may be defined by the circumferential position of the protrusion(s)/indentation(s) and/or the axial extent of the protrusion(s)/indentation(s) and/or the radial extent of the protrusion(s)/indentation(s) and/or the circumferential extent of the protrusion(s)/indentation(s). In one embodiment at least one of the circumferential position, the axial, radial and circumferential extents is used to designate a first feature of the medicament while at least one of the remaining of the circumferential position, the axial, radial and circumferential extents are used to designate a second feature of the medicament.

As an example the position of the indentations may be used to designate the kind of medicament and at least one of the radial, axial or circumferential extents may be used to designate the concentration of the medicament.

Accordingly, it will be appreciated that the medical delivery system according to the present invention provides a plurality of coding geometries each of which may be used to designate different features. As an example the first and second fastening means may be used to designate a first predetermined feature of the medicament such as its kind, and the axially extending coding mechanism may be used to designate a second predetermined feature of the medicament such as its concentration. Other examples of features which may be designated by a coding geometry are: male/female medication; child/adult medication; prophylactic/therapeutic medication, slow/fast acting medication.

In one embodiment the container comprises at least two protrusions, such as two, three or four, extending from the proximal end surface of the container and the dosing assembly comprises at least two indentations, such as two, three or four, adapted to cooperate with the at least two protrusions.

At least a part of said predetermined movement may be a concurrent axial and rotational movement. In one embodiment the predetermined movement defines a substantially pure axial movement and a subsequent combined concurrent axial and rotational movement. The substantially pure axial movement may be used to indicate to the user that the projection and the groove match, whereby it may be prevented that a user performs the combined movement with force causing the groove or the projection to be damaged.

Alternatively, or as a supplement, the predetermined movement defines the combined concurrent axial and rotational movement and a subsequent substantially pure rotational movement. The substantially pure rotational movement may be used to indicate to the user that the container and the dosing assembly are in fact fastened to each other.

The first/second fastening means and/or axially extending coding mechanism(s) may be adapted to prevent at least a part of the axial and/or rotational movement of the predetermined movement, so as to prevent coupling of the container to the dosing assembly. When the container cannot be coupled to the dosing assembly, the dosing assembly cannot be used to expel the medicament.

In one embodiment the container comprises a cartridge holder and a cartridge defining said chamber. The second fastening means may be defined by or attached to the cartridge holder. Moreover, the indentation(s)/protrusion(s) and/or the projection(s)/groove(s) may be defined by the cartridge holder. The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder, such that if the cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming a one element without seams. Such a monolithic element may be formed as a moulded article made of a synthetic resin such as Topas® or polypropylene. Such a moulded article may include the fastening and coding elements which are formed during moulding. However, any material which is suitable for long-term storage of the specific medication to be accommodated in the container may be used.

As describe in above at least a part of said predetermined movement may be a concurrent axial and rotational movement. Moreover, the first and/or second fastening means may be adapted to prevent a part of the axial and/or rotational movement of the predetermined movement, so as to prevent coupling of the container to the dosing assembly unless each of the first and second fastening means defines a predetermined asymmetric coding geometry. The coding geometry of the first and/or second fastening means may be is defined by at least one of: a circumferential extent of the first and second fastening means, an axial extent of the first and second fastening means, a radial extent of the first and second fastening means and the circumferential position of the first and second fastening means.

One embodiment comprises:
a first container having any of the abovementioned features and/or elements, which first container is adapted to be fastened to a first dosing assembly having any of the abovementioned features and/or elements; and
a second container having any of the abovementioned features and/or elements, which second container is adapted to be fastened to a second dosing assembly having any of the abovementioned features and/or elements; and
wherein at least two of:
the first fastening means of the first dosing assembly,
the first fastening means of the second dosing assembly,
the second fastening means of the first container, and
the second fastening means of the second container,
are adapted to prevent the first dosing assembly and second container from being fastened to each other, and to prevent the second dosing assembly and the first container from being fastened to each other.

Moreover, the predetermined movement required for coupling and uncoupling the first container to the first dosing assembly and for coupling the second container to the second dosing assembly may be essentially the same.

In a SECOND aspect the present invention relates to a container suitable for use (adapted to be used) in a medical delivery system according to the first aspect of the invention.

It will be appreciated that the invention according to the second aspect may comprise any feature and/or element of the invention according to the first aspect. In particular the container of the second aspect may comprise any feature and/or element of the container according to the first aspect of the invention.

In a THIRD aspect the present invention relates to a dosing assembly suitable for use (adapted to be used) in a medical delivery system according to the first aspect of the invention.

It will be appreciated that the invention according to the third aspect may comprise any feature and/or element of the invention according to the first aspect. In particular the dosing assembly of the third aspect may comprise any feature and/or element of the dosing assembly according to the first aspect of the invention.

DETAILED DESCRIPTION OF THE INVENTION

Figure 2:
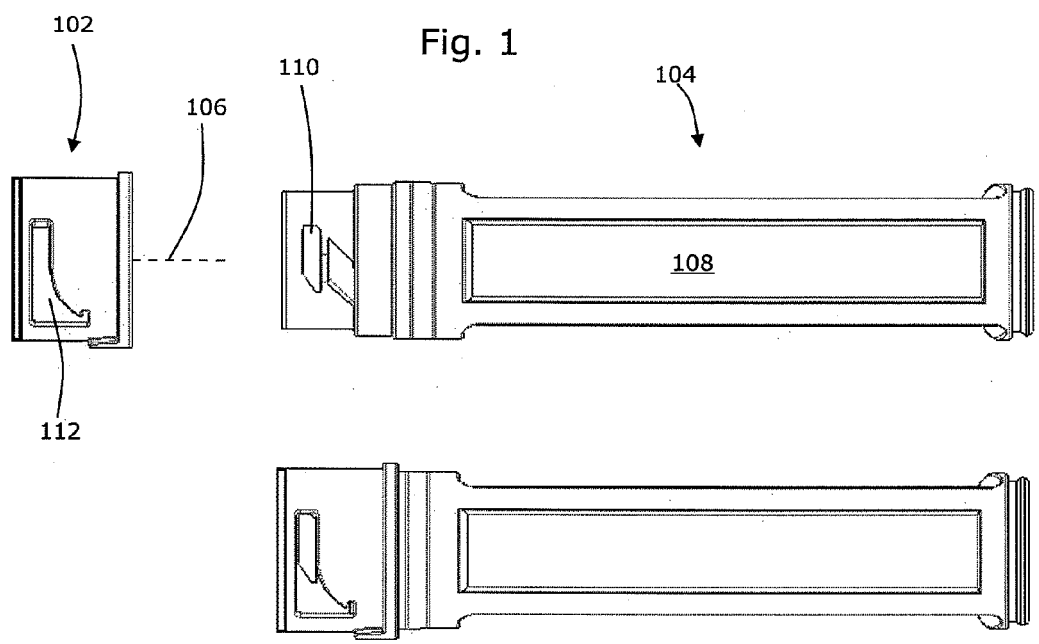
Figure 3:
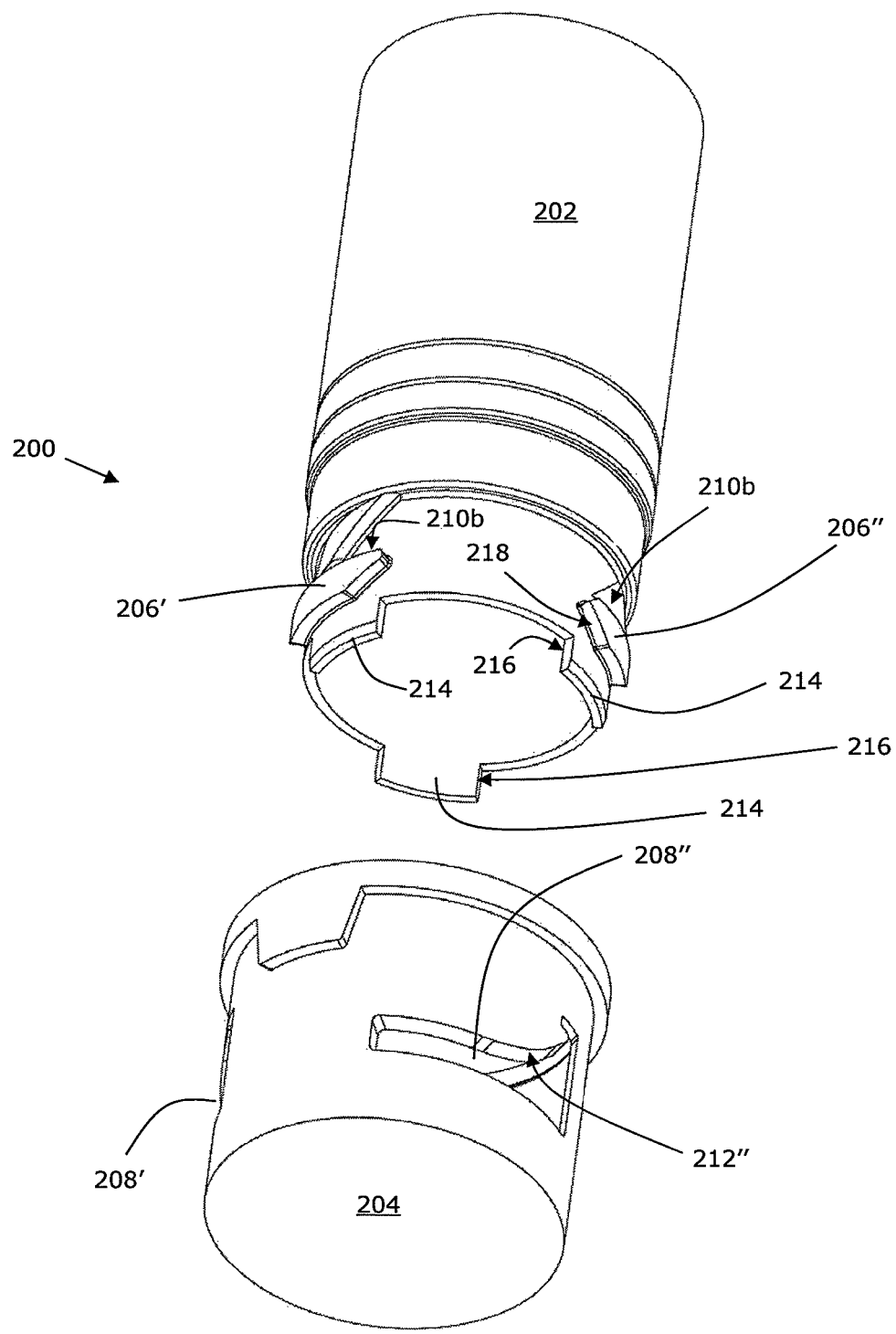
Figure 4:
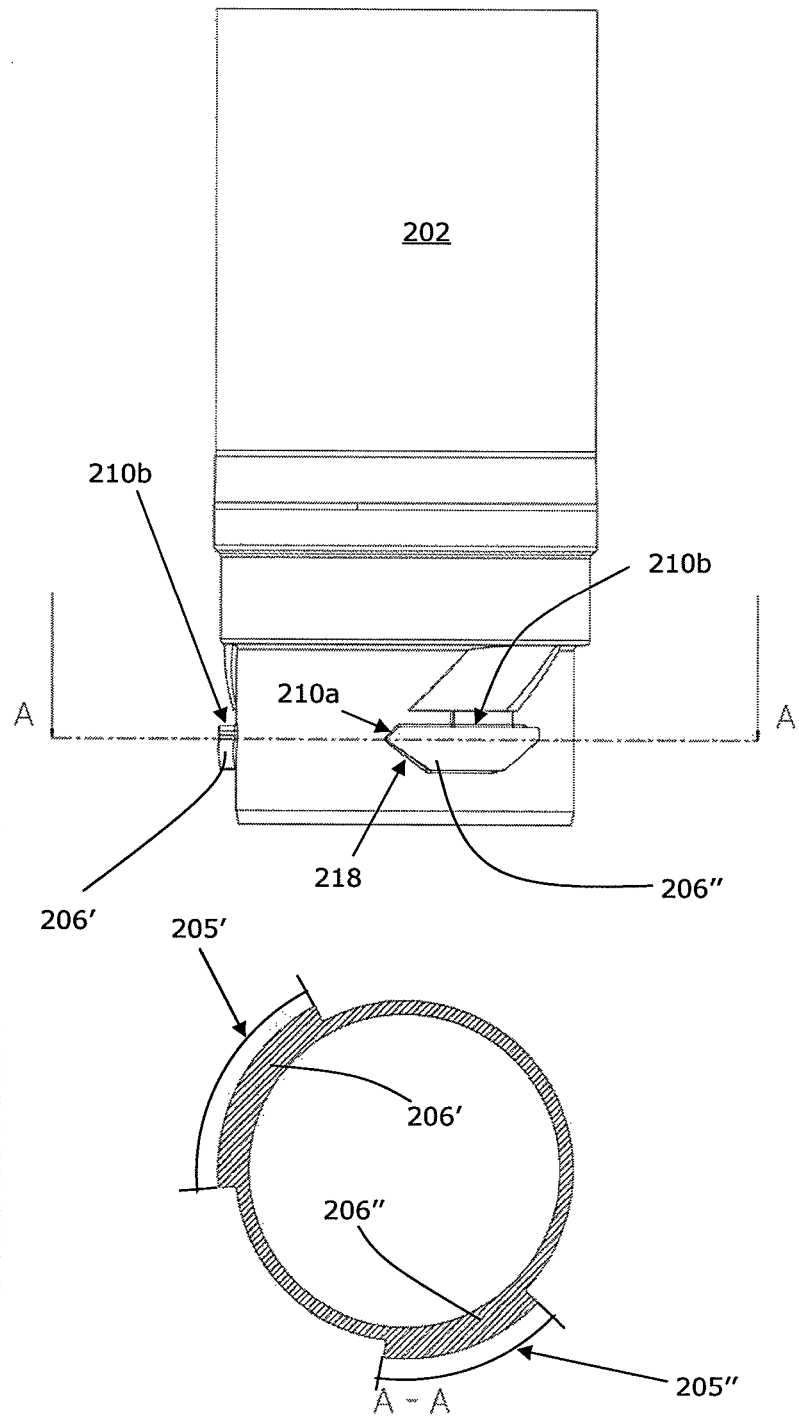
Figure 5:
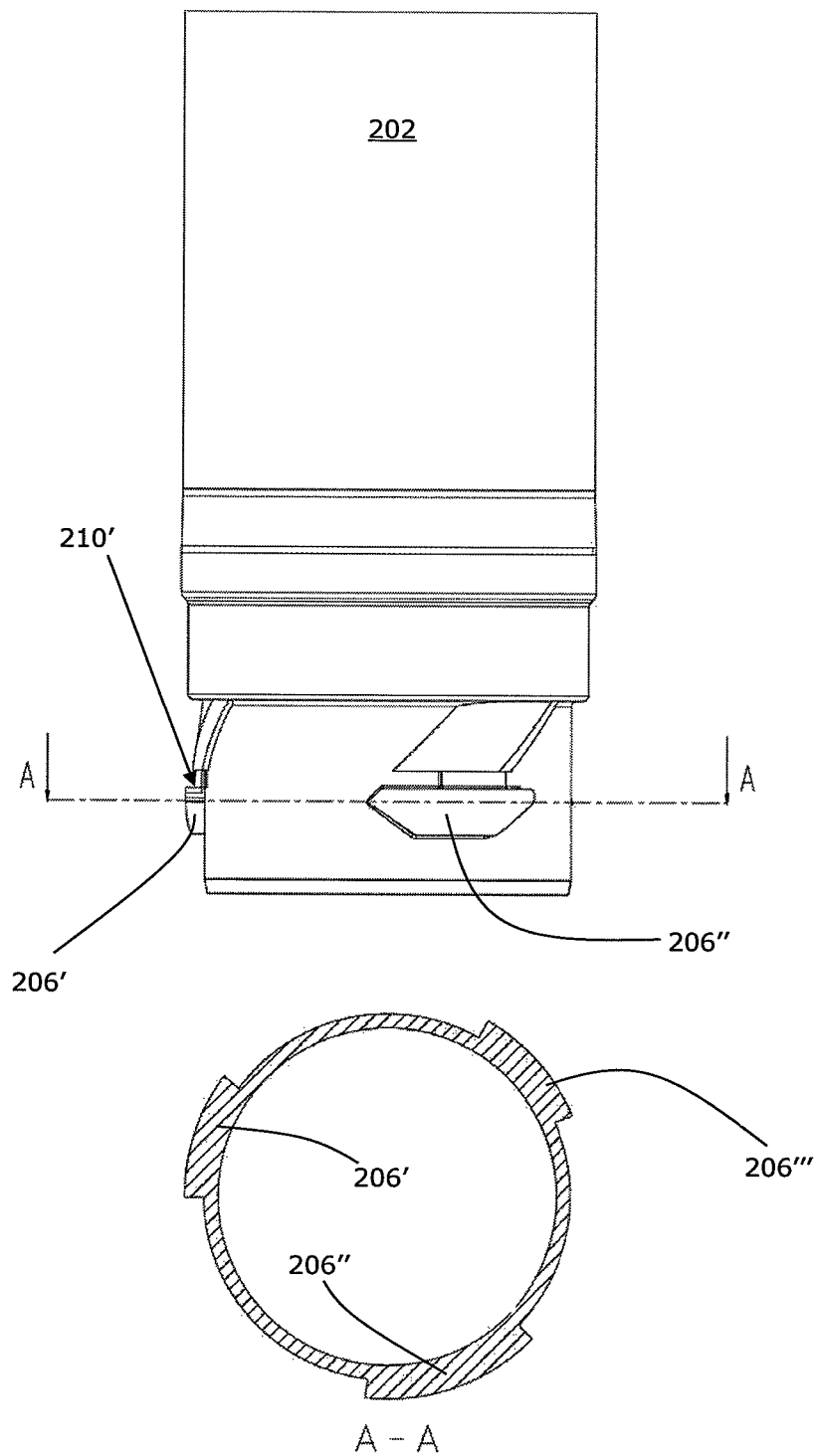

The invention will now be described in further detail with reference to the drawings in which:

FIGS. 1 and 2 disclose a syringe device known in the art,

FIG. 3 discloses a medical delivery system according to the present invention, and FIGS. 4 and 5 disclose a container having two and three projections respectively, FIGS. 6-12 disclose cross-sections of containers having two, three or four projections.

Figure 13A:
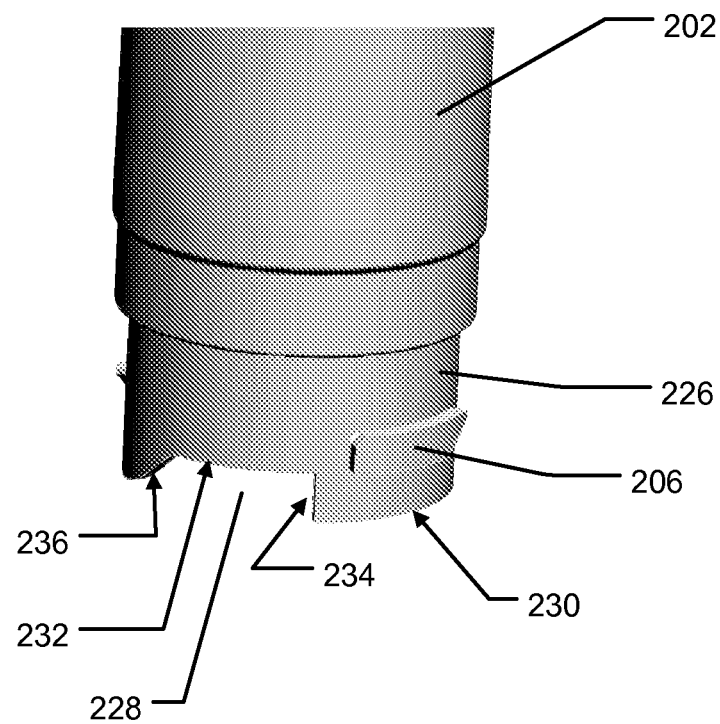
Figure 13B:
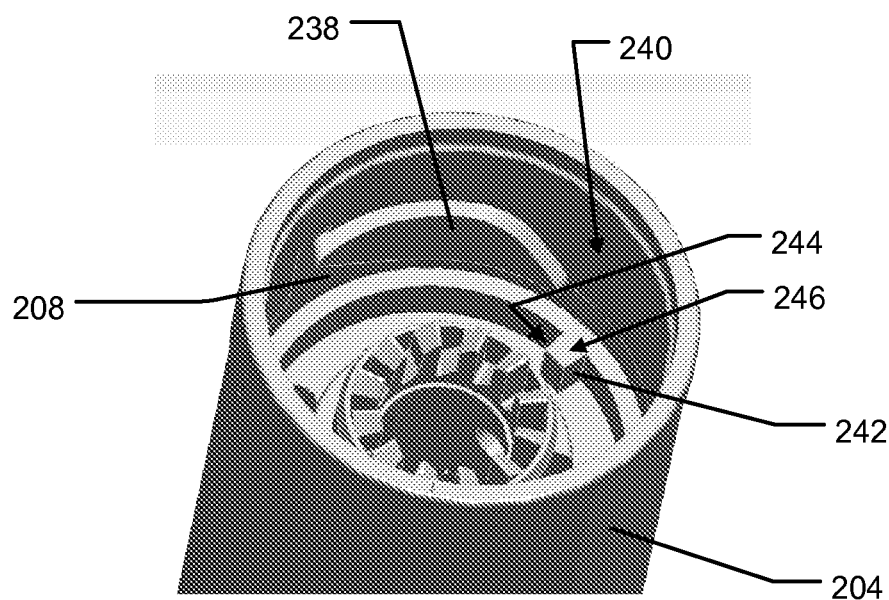

FIGS. 13a and 13b disclose an embodiment having axially extending indentations which during fastening are rotated into engagement with axially extending protrusions.

FIGS. 1 and 2 disclose a syringe device 100 which prior to filing of the present application has been marketed in Europe and the USA by the applicant and under the name "NovoPen® 4". The syringe device 100 comprises a proximal part 102 and a distal part 104. In use, the proximal part 102 forms part of a dose setting unit (not shown) comprising a piston rod (not shown) extending through a passage (not shown) of the proximal part 102. A centre axis of the piston rod coincides with the dotted line 106. In use the distal part 104 defines a compartment 108 for accommodation of a reservoir (not shown) accommodating a medicament. The distal part 104 comprises two ridges 110 one on each side of the distal part which are used to secure the distal part 104 to the proximal part 102, by advancing the ridges 110 into matching tracks 112 of the proximal part 102. The tracks are defined on an inner surface 114 of the proximal part 102.

FIG. 3 discloses a medical delivery system 200 comprising a container 202 and a dosing assembly 204 (for simplicity reasons only a part of the dosing assembly is disclosed). The container 202 defines two projections 206',206" which are adapted to engage matching grooves 208',208" of the dosing assembly 204. When the projections 206',206" are advanced into the grooves 208',208", the container and the dosing assembly may be rotated whereby the engagement between a distal facing surface 210a of container and a proximal facing surface 212 of dosing assembly 212 causes the dosing assembly and the container to be pulled towards each other while performing a concurrent axial and rotational movement. The concurrent movement is caused by the sloping proximal facing surface 212 which initially engages distal facing surface 210a and subsequently distal facing surface 210b.

The medical delivery system comprises three axially extending protrusions 214, which in a first embodiment of FIG. 3 define rotational stopping surfaces 216 which during the concurrent movement are adapted to engage corresponding stopping surfaces (not shown) of the dosing assembly so as to prevent further rotational movement.

In a second embodiment of FIG. 3 the protrusions 214 define a first part of an axially extending coding mechanism which further comprises axially extending indentations (not shown) provided in the dosing assembly.

The projections 206',206" comprises two inclined surfaces 218 which prevents unintentional engagement between a projection and a groove e.g. in the case of a patient trying to fasten a container to a dosing assembly to which it cannot be fastened. Thus, should the user tilt the container and the dosing assembly (such that their longitudinal axes are not coincide but rather cross each other) whereby a single projection could be advanced into a groove, relative rotation between the container and the dosing assembly causes the projection to be forced out of the groove due to the inclined surfaces 218.

FIG. 4 discloses a cross-section and an elevational view of a container 202 which comprises two projections 206',206" provided in an asymmetrical pattern which is disclosed in the cross-sectional view of FIG. 5 and which comprises no lines of symmetry. The circumferential extent 205' of the first projection 206' is larger than the circumferential extent 205" of the second projection 206". Due the asymmetry the container can only be fastened to a matching dosing assembly when the container is positioned in one single predetermined rotational position relative to the dosing assembly.

FIG. 5 discloses a cross-section and an elevational view of a container 202 having three projections 206',206",206'''. The projections define no lines of symmetry and the circumferential extent of the first projection 206' is larger than the circumferential extent of the third projection 206''' which again is larger than the circumferential extent of the second projection 206''.

Figure 6:
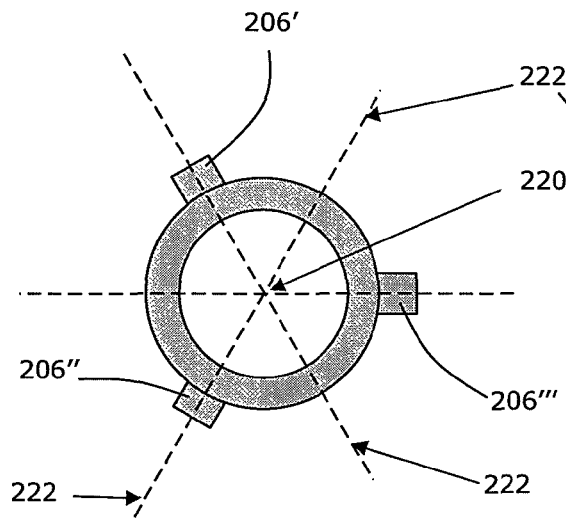
Figure 7:
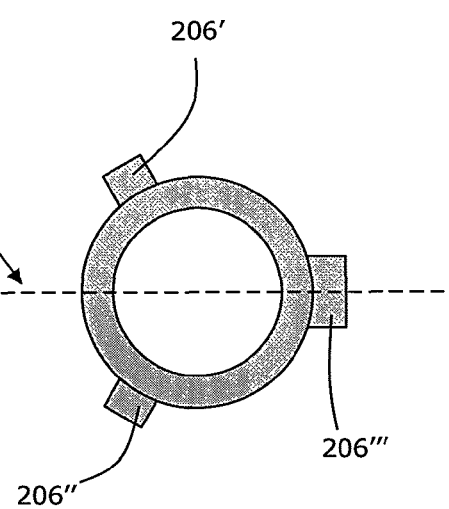
Figure 8:
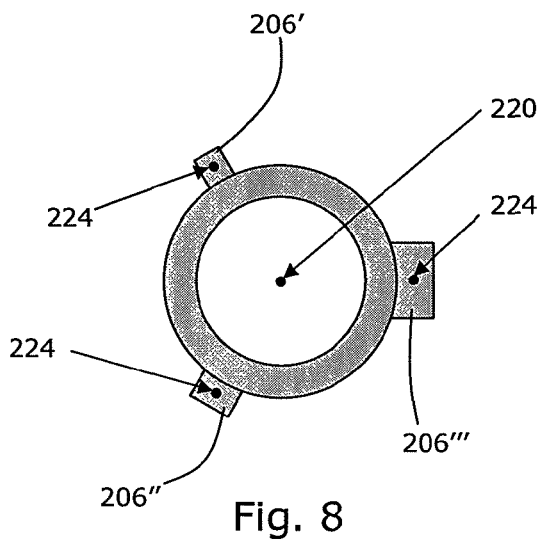

FIGS. 6-8 disclose three containers each of which comprises three projections 206',206'',206'''. In FIG. 6 the angle between any two projections (about a centre axis 220) is 120 degrees and the projections have identical shapes. The cross section of the container defines three lines of symmetry 222. In FIG. 7 the first and second projection 206',206'' have identical shapes whereas the shape of the third projection 206''' is different from the first and second projection. Again the angle between the any two projections is 120 degrees and the container defines one line of symmetry 222. In the third embodiment the first projection 206' is larger than the second projection 206'' which is larger than the third projection 206''' and thus the cross section defines no line of symmetry.

The projections may define a centre point 224 as disclosed in relation to FIG. 8. The centre point may be defined as the centre of inertia of the projections and in FIG. 8 the angle between any of the centre points about the centre axis 220 is 120 degrees and thus different from 180 degrees.

Figures 9, 10:
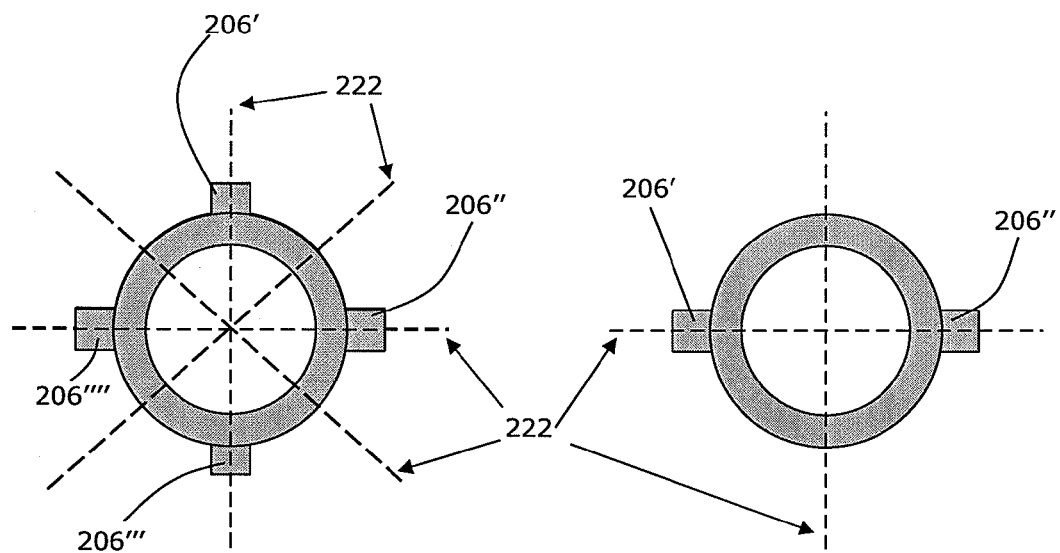

The container of FIG. 9 comprises four projections 206', 206'',206''',206''' rotationally spaced by 90 degrees. As the projections furthermore have identical shapes the cross-section of the container defines four lines of symmetry 222. The container of FIG. 10 comprises two projections 206',206'' and thus define two lines of symmetry.

Figures 11, 12:
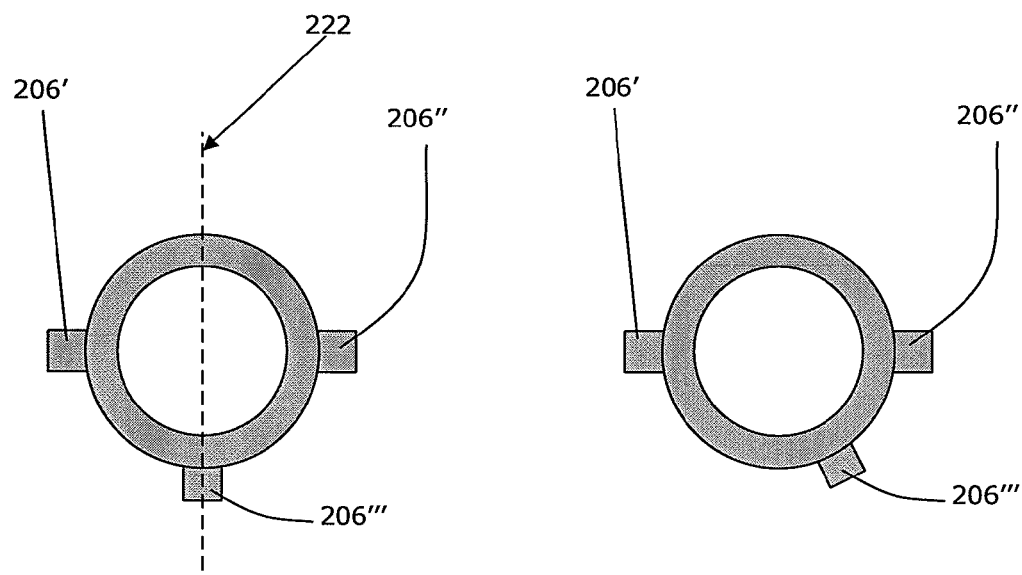

In FIG. 11 the container comprises three identical projections 206',206'',206''' and defines one line of symmetry. Moreover, the single line of symmetry extend through one of the projections. In FIG. 12 the position of one of the projections is changed relative to the container of FIG. 11 whereby the container defines on lines of symmetry.

The container 202 of FIG. 13a is adapted to be fastened to the dosing assembly 204 of FIG. 13b, through a combined rotational and axial movement. The container 202 defines a radially extending projection 206 which extends from a sidewall 226 of the container 202, and an indentation 228 extending axially into the sidewall 226, in a distal direction from the proximal end surface 230. The axially extending indentation 228 defines a bottom surface 232, a stop surface 234 and an inclined surface 236. The dosing assembly 204 defines a groove 208 for receiving the projection 206 during fastening of the container 202 to the dosing assembly 204. In the embodiment of FIG. 13b the groove 208 is defined by a projection 238 extending radially out from a sidewall 240 of the dosing assembly 204 and in the direction of the centre of the dosing assembly 204. The inclined surface 236 is shaped so as to allow an axially extending protrusion 242 of the dosing assembly 204 to be moved into (and thus received by) the axially extending indentation 228 of the container 202. The stop surface 234 of the indentation 228 is adapted to engage a corresponding stop surface 244 of the protrusion 242 of the dosing assembly 204 so as to prevent further relative rotation between the container 202 and the dosing assembly 204. Abutment between the two stop surfaces 234, 244 provides the user with a tactile indication of the fact that the container 202 is fastened to the dosing assembly 204.

The projection 238 of the dosing assembly is shaped such that the groove 208 does not define a stop surface and thus a dosing assembly similar to that of FIG. 13b but without the axially extending protrusion 242, will not provide the user with a tactile indication of the fact that the container 202 is fastened to such a dosing assembly 204. Accordingly, the container 202 of FIG. 13a cannot be fastened to a dosing assembly 204 similar to that of FIG. 13b but not defining the protrusion 242. This prevents a container 202 from being fastened to a dosing assembly 204 of that configuration.

Containers similar to that of FIG. 13a but not defining the axially extending indentation 228 may take two forms. A first form wherein the proximal end surface 230 is defined at the same axial level as the surface 230 in FIG. 13a, and a second wherein the proximal end surface 230 is defined at the same axial level as the bottom surface 232 in FIG. 13a. The difference between the first and the second forms is the distance between surface 230 and the projection 206.

A container 202 of the first form i.e. wherein the proximal end surface 230 is defined at the level same axial level as the proximal end surface 230 of FIG. 13a and without indentations 228, cannot be fastened to the dosing assembly 204 of FIG. 13b as the proximal end surface 230 of the container 202 will abut a distal facing surface 246 of the protrusion 242, whereby the projection 206 cannot be received in the groove 208 or can only be moved partly into the groove 208 i.e. in a way insufficient to fasten the container 202 to the dosing assembly 204.

A container 202 of the second form i.e. wherein the proximal end surface 230 is defined at the same axial level the bottom surface 232 in FIG. 13a and not defining indentations 228, cannot be fastened to a dosing assembly 204 not defining the axially extending protrusion(s) 242 as the user is not provided with the tactile indication allowing him to determine when the container 202 is fastened to the dosing assembly 204 and vice versa. Accordingly, the user will continue the relative rotation between the container 202 and the dosing assembly 204, whereby the projection 206 will be moved out of the groove 208, such that the container 202 is not fastened to the dosing assembly 204.

It will be appreciated from the above, that the embodiment of FIG. 13a and 13b increases user safety as a container 202 not designated to be used in connection with a predetermined dosing assembly 204, cannot be fastened to such a dosing assembly 204. Thus, the user is prohibited from attaching a container 202 with a wrong medicament or a correct medicament in a wrong concentration to a dosing assembly 204, and thereby prevented from ejecting such a medicament.

The invention claimed is:
1. A medical delivery system comprising:
   a container structured to house a medicament in a chamber defined by the container and a slidably arranged piston which is moveable in a distal direction towards an outlet so as to reduce the volume of the chamber and expel the medicament through the outlet;
   a dosing assembly adapted to be fastened to the container, so as to allow a driver of the dosing assembly to move the piston of the container in the distal direction;
   wherein the dosing assembly defines a substantially proximal facing surface of a first fastening means which during fastening of the container to the dosing assembly engages a substantially distal facing surface of a second fastening means of the container whereby the container is fastened to the dosing assembly through a predetermined movement defined by at least one of the first and the second fastening means, the predetermined movement being less than one revolution;
   wherein a sidewall of the second fastening means defines at least two projections extending in a radially outward direction, each of the at least two projections being adapted to engage a corresponding groove defined in a sidewall of the first fastening means;

wherein the second fastening means defines an asymmetrical pattern defining no line of symmetry in a plane transverse to an axial direction of the device; and wherein the system further comprises an axially extending coding mechanism extending from and defined by a proximal end surface of the container and a corresponding distal end surface of the dosing assembly.

2. A medical delivery system according to claim 1, wherein each of the first and second fastening means defines an asymmetrical pattern in the plane transverse to the axial direction of the device.

3. A medical delivery system according to claim 1, wherein at least one of the first and second fastening means defines less than two lines of symmetry in the plane transverse to the axial direction of the device.

4. A medical delivery system according to claim 1, wherein at least the first fastening means defines no line of symmetry in the plane transverse to the axial direction of the device.

5. A medical delivery system according to claim 1, wherein the plane extends through all of the at least two projections or the at least two grooves.

6. A medical delivery system according to claim 1, wherein each of the at least two projections or grooves defines a centre point, and wherein the angle between any two centre points about the longitudinal axis of the device, is different from 180 degrees.

7. A medical delivery system according to claim 1, wherein the circumferential extent of two or more of the at least two projections or grooves are different.

8. A medical delivery system according to claim 1, wherein one or more of the at least two projections or grooves define an inclined surface.

9. A medical delivery system according to claim 1, wherein the proximal end surface of the container defines one or more axially extending protrusions and/or indentations which during fastening of the container to the dosing assembly cooperate(s) with matching one or more protrusions and/or indentations of a distal facing coding surface of the dosing assembly so as to prevent said predetermined movement unless each of the distal and proximal facing surfaces define one or more predetermined protrusions and/or indentations selected from a predetermined group of protrusions and/or indentations.

10. A medical delivery system according to claim 1, wherein the container comprises a cartridge holder defining said second fastening means, and a cartridge defining said chamber, and wherein the cartridge is non-detachably attached to the cartridge holder.

11. A medical delivery system according to claim 1, wherein at least a part of said predetermined movement is a concurrent axial and rotational movement.

12. A medical delivery system according to claim 11, wherein the first and/or second fastening means is/are adapted to prevent a part of the axial and/or rotational movement of the predetermined movement, so as to prevent coupling of the container to the dosing assembly unless each of the first and second fastening means defines a predetermined coding geometry.

13. A medical delivery system according to claim 12, wherein the coding geometry of the first and/or second fastening means is defined by at least one of: a circumferential extent of the first and second fastening means, an axial extent of the first and second fastening means, a radial extent of the first and second fastening means and the circumferential position of the first and second fastening means.

14. A medical delivery system comprising:
a first container and a second container each structured to house a medicament in a chamber defined by the container and a slidably arranged piston which is moveable in a distal direction towards an outlet so as to reduce the volume of the chamber and expel the medicament through the outlet,
a first dosing assembly and a second dosing assembly, each structured to allow a driver of the dosing assembly to move the piston of the container in the distal direction, wherein each dosing assembly defines a substantially proximal facing surface of a first fastening means which during fastening of the container to the dosing assembly engages a substantially distal facing surface of a second fastening means of the container whereby the container is fastened to the dosing assembly through a predetermined movement defined by at least one of the first and the second fastening means, the predetermined movement being less than one revolution, wherein a sidewall of the second fastening means defines at least two projections extending in a radially outward direction, and wherein the second fastening means defines an asymmetrical pattern defining no line of symmetry in a plane transverse to an axial direction of the device, and wherein the system further comprises an axially extending coding mechanism extending from defined by a proximal end surface of the container and a corresponding distal end surface of the dosing assembly, and
wherein at least two of:
the first fastening means of the first dosing assembly,
the first fastening means of the second dosing assembly,
the second fastening means of the first container, and
the second fastening means of the second container, are adapted to prevent the first dosing assembly and second container from being fastened to each other, and to prevent the second dosing assembly and the first container from being fastened to each other.

15. A medical delivery system according to claim 14, wherein the predetermined movement required for coupling and uncoupling the first container to the first dosing assembly and for coupling the second container to the second dosing assembly are essentially the same.

16. A container for a medical delivery system structured to house a medicament in a chamber defined by the container and a slidably arranged piston which is moveable in a distal direction towards an outlet so as to reduce the volume of the chamber and expel the medicament through the outlet;
wherein the container is adapted to fasten to a dosing assembly of the medical delivery system through a predetermined movement defined by at least one of a first and a second fastening means, the predetermined movement being less than one revolution;
wherein a sidewall of the second fastening means defines at least two projections extending in a radially outward direction, each of the at least two projections being adapted to engage a corresponding groove defined in a sidewall of the first fastening means;
wherein the second fastening means defines an asymmetrical pattern defining no line of symmetry in a plane transverse to an axial direction of the device; and
wherein the system further comprises an axially extending coding mechanism extending from and defined by a proximal end surface of the container.

17. A dosing assembly suitable for use in a medical delivery system according to claim 1.

* * * * *